(12) United States Patent
Taguchi et al.

(10) Patent No.: US 7,517,692 B2
(45) Date of Patent: Apr. 14, 2009

(54) TEMPERATURE ADJUSTING METHOD FOR ANALYTICAL TOOL AND ANALYTICAL DEVICE HAVING TEMPERATURE ADJUSTMENT FUNCTION

(75) Inventors: Takayuki Taguchi, Kyoto (JP); Shigeru Kitamura, Kyoto (JP)

(73) Assignee: Arkray, Inc., Kyoto (JP)

( * ) Notice: Subject to any disclaimer, the term of this patent is extended or adjusted under 35 U.S.C. 154(b) by 684 days.

(21) Appl. No.: 10/513,861

(22) PCT Filed: Apr. 28, 2003

(86) PCT No.: PCT/JP03/05480

§ 371 (c)(1),
(2), (4) Date: Oct. 29, 2004

(87) PCT Pub. No.: WO03/093835

PCT Pub. Date: Nov. 13, 2003

(65) Prior Publication Data

US 2005/0164401 A1    Jul. 28, 2005

(51) Int. Cl.
*G01N 25/00* (2006.01)
*G01N 21/00* (2006.01)

(52) U.S. Cl. .................. 436/147; 436/164; 436/174; 422/82.05; 422/82.12; 422/109

(58) Field of Classification Search .............. 436/55, 436/164, 171, 172, 174, 805, 807, 808, 147; 422/109, 55, 58, 82.05, 82.12; 73/863.11
See application file for complete search history.

(56) References Cited

U.S. PATENT DOCUMENTS

| 4,446,719 | A | * | 5/1984 | Lambert | .................. 73/24.02 |
| 4,859,420 | A | * | 8/1989 | Schultz | ...................... 422/58 |
| 4,927,766 | A | * | 5/1990 | Auerbach et al. | ............. 436/44 |
| 5,023,187 | A | * | 6/1991 | Koebler et al. | ............. 436/180 |
| 5,681,529 | A | | 10/1997 | Taguchi et al. | |
| 5,869,346 | A | * | 2/1999 | Xiaoming et al. | ........... 436/525 |
| 6,210,882 | B1 | * | 4/2001 | Landers et al. | ................ 435/6 |
| 6,297,057 | B1 | * | 10/2001 | Kawamura et al. | ........... 436/86 |
| 6,303,386 | B2 | * | 10/2001 | Klimant et al. | ............. 436/172 |

(Continued)

FOREIGN PATENT DOCUMENTS

JP     8-114539    5/1996

(Continued)

*Primary Examiner*—Duane Smith
*Assistant Examiner*—Robert A Clemente
(74) *Attorney, Agent, or Firm*—Hamre, Schumann, Mueller & Larson, P.C.

(57) ABSTRACT

The present invention relates to a technique for causing the temperature of a liquid component retained in an analytical tool (1) to be adjusted to a target temperature, wherein the analytical tool (1) is used for analyzing the sample. According to the present invention, the temperature of the liquid component (10) is raised by heating the liquid component utilizing light energy from a light source (23). The temperature raising of the liquid component may be performed by supplying the light energy directly to the liquid component. Alternatively, the temperature raising of the liquid component may be performed by thermal energy transferred from a temperature raise region adjacent to the liquid component to which the light energy supplied. Preferably, as the light source (23) for raising temperature, use may be made of a laser diode or a light-emitting diode.

19 Claims, 8 Drawing Sheets

U.S. PATENT DOCUMENTS

| | | | |
|---|---|---|---|
| 6,326,211 B1 * | 12/2001 | Anderson et al. | 436/177 |
| 6,503,457 B1 * | 1/2003 | Neeper et al. | 422/102 |
| 6,734,436 B2 * | 5/2004 | Faris et al. | 250/432 R |
| 6,833,536 B2 * | 12/2004 | Shigeura | 219/553 |
| 7,173,218 B2 * | 2/2007 | Shigeura et al. | 219/428 |
| 2003/0035755 A1 * | 2/2003 | Chen et al. | 422/52 |
| 2004/0053418 A1 * | 3/2004 | Fouillet et al. | 436/164 |
| 2005/0148091 A1 * | 7/2005 | Kitaguchi et al. | 436/164 |

FOREIGN PATENT DOCUMENTS

| | | |
|---|---|---|
| JP | 9-189703 | 7/1997 |
| JP | 9-304269 | 11/1997 |
| JP | 10-253536 | 9/1998 |
| JP | 2002-1102 | 1/2002 |
| JP | 2002-90357 | 3/2002 |
| JP | 2002-102681 | 4/2002 |

* cited by examiner

TEMPERATURE ADJUSTING METHOD FOR ANALYTICAL TOOL AND ANALYTICAL DEVICE HAVING TEMPERATURE ADJUSTMENT FUNCTION

TECHNICAL FIELD

The present invention, applicable to analytic tools used for sample analysis, relates to a technique for adjusting the temperature of a liquid component retained in an analytical tool, so that the temperature attains a desired value.

BACKGROUND ART

Sample analysis can be performed by optically analyzing the reaction liquid obtained from the sample and a reagent reacting thereupon. For performing such an analysis, an analytical tool to provide a reaction field is mounted to an analyzing device that constitutes an optical system in which light emission and light reception are possible (See JP-A-8-114539, for example). In this case, to reduce the analysis error and improve the reliability of the analysis results, it is preferable to adjust the temperature of the analytical tool (particularly, the reaction solution) so that the sample reacts with the reagent at a generally constant temperature for each measurement. Particularly, in a system which utilizes enzyme reaction, the reaction speed largely depends on temperature. Therefore, the temperature of this system is controlled to e.g. ±0.1° C. relative to a prescribed target temperature.

FIG. 9A shows an example of method for adjusting temperature of a reaction solution. In this method, an analytical tool 9 is held on a heat block 91 having a heat capacity larger than that of a reaction solution 90, and the temperature of the heat block 91 is controlled for adjusting the temperature of the reaction solution 90 See JP-A-9-189703 and JP-A-10-253536, for example). In this method, a temperature sensor 92 embedded in the heat block 91 monitors the temperature of the reaction solution 90. When the temperature of the reaction solution 90 drops below a predetermined value, the heat block 91 is heated for raising the temperature, whereby the temperature of the reaction solution 90 is raised via the heat block 91. FIG. 9B shows another method, in which an analytical tool 9 is held on a heating element 93 which has an excellent temperature-tracking property. In this method, the temperature of the reaction solution 90 is directly adjusted by the heating element 93 (See JP-A-9-304269, for example). In this method again, the heating element 93 is driven in accordance with the monitoring results of the temperature sensor 92, whereby the temperature of the reaction solution 90 is adjusted.

In the above temperature adjustment methods, it is necessary to heat the heat block 91 or to drive the heating element 93 in raising the temperature of the reaction solution 90, which disadvantageously leads to high power consumption. Further, when the amount of the liquid component 90 is small as is in a micro-device, pinpoint heating of the region where the reaction solution 90 is retained cannot be performed easily by the use of a heating medium such as the heat block 91 or the heating element 93. Therefore, to raise the temperature of the liquid component 90 with high response, the heating medium 91, 93 need be made considerably large as compared with the region whose temperature is to be raised (the region directly below the reaction solution 90 in the figure). Therefore, the amount of heat utilized for raising the temperature of the reaction solution 90 relative to the amount of heat conducted from the heating medium 91, 93 becomes small, and the energy cannot be utilized efficiently.

As noted above, prior art temperature adjustment methods have disadvantages such as high power consumption and inefficient energy utilization. Therefore, it is difficult to apply the prior art temperature adjustment methods to an analyzing device driven by an internal power source such as a small battery (like one widely used at home, for example). Even the application of such methods to a small analyzing device is possible, it is not practical because the operating time of the analyzing device is considerably shortened. Although shortening of the operating time may be prevented by increasing the capacity of the internal power source, such an increase hinders the size reduction of the analytical tool, whereby convenience in carrying is reduced. When electric power is to be supplied from an external power source, an adapter for connecting the analyzing device to the external power source is necessary, which reduces the convenience in carrying and hinders the use when away from home.

DISCLOSURE OF THE INVENTION

An object of the present invention is to adjust the temperature of a liquid component retained in an analytical tool to a target temperature with low power consumption and without increasing the size of the analyzing device.

According to a first aspect of the present invention, there is provided a temperature adjustment method for an analytical tool used for analyzing a sample. A liquid component retained in the analytical tool is adjusted to the prescribed target temperature. When a temperature raise is required for the liquid component, light energy from a light source is utilized for heating the liquid component.

According to a second aspect of the present invention, there is provided an analyzing device which utilizes an analytical tool with a sample retained thereon for analyzing the sample, wherein the analyzing device has a function for adjusting the temperature of the liquid component retained on the analytical tool. To this end, the analyzing device comprises a temperature-raising light source for raising the temperature of the liquid component.

Preferably, the analyzing device may further comprise: a temperature measurer for measuring the temperature of the liquid component or the ambient temperature around the liquid component; and a light source controller for controlling the temperature-raising light source in accordance with the measurements obtained from the temperature measurer.

In the present invention, the "liquid component" refers to a liquid retained in the analytical tool and serving as the target of the temperature adjustment. Unless otherwise mentioned, it may indicate all the kinds of liquids existing on the analytical tool or only a selected kind or kinds of the liquids. For example, in a system where a sample liquid is reacted with a reagent liquid, the "liquid component" may refer to only one of the sample liquid, the reagent liquid and the reaction liquid, or may refer to more than one of them. Further, when one of the sample liquid, the reagent liquid and the reaction solution is solely indicated, the liquid component may refer to only a part of the liquid that exists at a particular region.

According to the present invention, the temperature raising of the liquid component may be performed by directly supplying the light energy to the liquid component or by supplying the light energy to a temperature raise region provided adjacent to the liquid component and transferring thermal energy from the temperature raise region. The former method is advantageous in that the light energy can be utilized efficiently because of the direct supply of the light energy. To properly raise the temperature of the liquid component, however, irradiation of near-infrared rays or infrared rays which have high absorptance to water is preferable. In particular, use may be made of irradiation of near-infrared rays or infrared rays of 950-1000 nm, about 1100 nm, 1400-1500 nm, 1850-2100 nm or about 2500 nm. In the latter method, various kinds of material can be used as the material for forming the temperature raise region as long as it can absorb light and conduct the energy to the liquid component. Therefore, the material for constituting the temperature raise region can be selected from a wide range, and the wavelength of the light to be emitted can be selected depending on the light absorption characteristics of the material constituting the temperature raise region. Therefore, as compared with the former method in which light energy is directly supplied, the latter method is more advantageous in that the light source can be advantageously selected from a wider range.

As the light source, use may be made of a laser diode (LD) or a light-emitting diode (LED). Among these, a laser diode (LD) is more preferable, because an LD can perform pinpoint light irradiation and hence pinpoint heating whereby the light energy can be utilized efficiently. However, when an LD or an LED is used as the heating light source, it is difficult to adjust the temperature of a large amount of liquid component with high responsiveness. Therefore, it is preferable that the amount of liquid component as a temperature adjustment target is set to no more than 100 μL, for example. The temperature adjustment of a larger amount of liquid component can be performed by increasing the number of the LDs or LEDs.

The temperature adjustment of the liquid component may be performed by monitoring the temperature of the liquid component, feeding back the monitoring results, and repetitively controlling the light energy emitted from the light source. Alternatively, the adjustment may be performed by examining, in advance, the relationship between an ambient temperature around the liquid component and a controlled variable for the light source necessary for raising the temperature of the liquid component to the target temperature, determining the controlled variable of the light source based on a measured ambient temperature and the relationship, and controlling the light source in accordance with the controlled variable.

The temperature adjustment of the present invention can be applied to an analytical tool which is designed to analyze the sample based on a response obtained upon irradiation of light. In this case, the temperature-raising light source may be utilized as a light source for performing the sample analysis.

According to the present invention, the analytical tool may be a micro-device capable of analyzing a minute amount of sample. The present invention is also applicable to the case where analysis is performed by utilizing an analytical tool designed to analyze a sample by an electrochemical method.

BEST MODE FOR CARRYING OUT THE INVENTION

Preferred embodiments of the present invention will be described below in detail with reference to the accompanying drawings.

Figure 1:
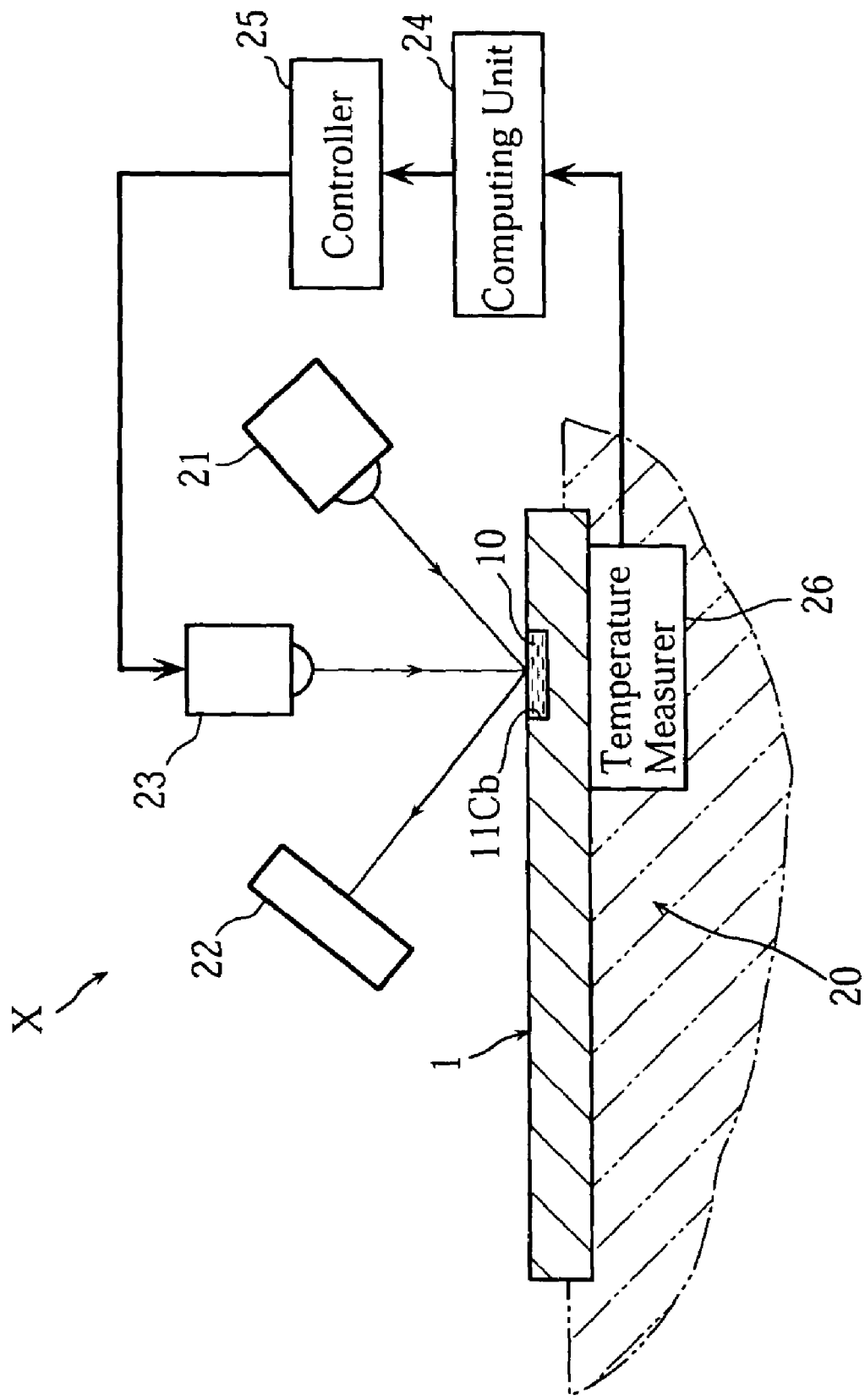
FIG. 1 is a schematic view showing the structure of an example of analyzing device according to the present invention.

An analyzing device X shown in FIG. 1 has an analysis function for analyzing a sample by using an analytical tool 1, and a temperature adjustment function for adjusting the temperature of a liquid component 10 retained at a measurement portion 11Cb of the analytical tool 1. The analyzing device includes a mount portion 20, a measurement light source 21, a light receiver 22, a heating light source 23, a computing unit 24, and a controller 25.

The mount portion 20 serves to hold the analytical tool 1. A temperature measurer 26 for measuring the temperature of the liquid component 10 retained in the analytical tool 1 is embedded in the mount portion 20. The temperature measurer 26 is so arranged as to be located directly below the liquid component 10 (measurement portion 11Cb) retained in the analytical tool 1 when the analytical tool 1 is mounted to the mount portion 20. With such an arrangement, the temperature measured by the temperature measurer 26 becomes close to the actual temperature of the liquid component 10.

As the temperature measurer 26, use may be made of a contact-type thermometer such as a thermistor or a thermocouple. Alternatively, a non-contact thermometer such as a radiation thermometer may be used. In this case, the temperature measurer 26 need not necessarily be embedded in the mount portion 20.

The measurement light source 21 serves to irradiate the liquid component 10 (measurement portion 11Cb) with light, whereas the light receiver 22 serves to receive the reflected light from the liquid component 10. The measurement light source 21 may comprise a mercury lamp or a white LED, for example. When such a light source is used, the light from the measurement light source 21 is caused to pass through a filter before reaching the liquid component 10, though the filter is not shown in the figure. The filter is used to select the light of a wavelength range which is appropriate for the light absorption characteristics of the analysis target component contained in the liquid component 10. Alternatively, the measurement light source 21 may comprise a laser diode (LD) or a light-emitting diode (LED) capable of emitting light of a single wavelength. The light receiver 22 may comprise a photodiode, for example.

The heating light source 23 serves to directly supply light energy to the liquid component 10 to raise the temperature of the liquid component 10. As the heating light source 23, any kind of light source can be used as long as it can raise the temperature of the liquid component 10. For example, use may be made of one that emits near-infrared rays or infrared rays which have high absorptance to water, and preferably one that emits near-infrared rays or infrared rays of 950-1000 nm, about 1100 nm, 1400-1500 nm, 1850-2100 nm or about 2500 nm. However, in view of the driving power, it is preferable that the heating light source 23 comprises a laser diode (LD) or a light-emitting diode (LED). Particularly, the use of a laser diode is preferable, because an LD can perform pinpoint light irradiation and hence pinpoint heating so that the light energy can be utilized efficiently.

The computing unit 24 computes the amount of energy to be applied to the liquid component 10 based on the measurements by the temperature measurer 26. Based on the computed value it also calculates the controlled variable for the heating light source 23. Based on such computations of the computing unit 24, the controller 25 switches on or off the heating light source 23. When the light source 23 is turned on, the controller controls the strength of the light emitted from the light source.

The computing unit 24 and the controller 25 may comprise a CPU, a ROM and a RAM, for example. In such a case, utilizing the RAM, the CPU executes a program stored in the ROM for controlling the heating light source 23.

Figure 2:
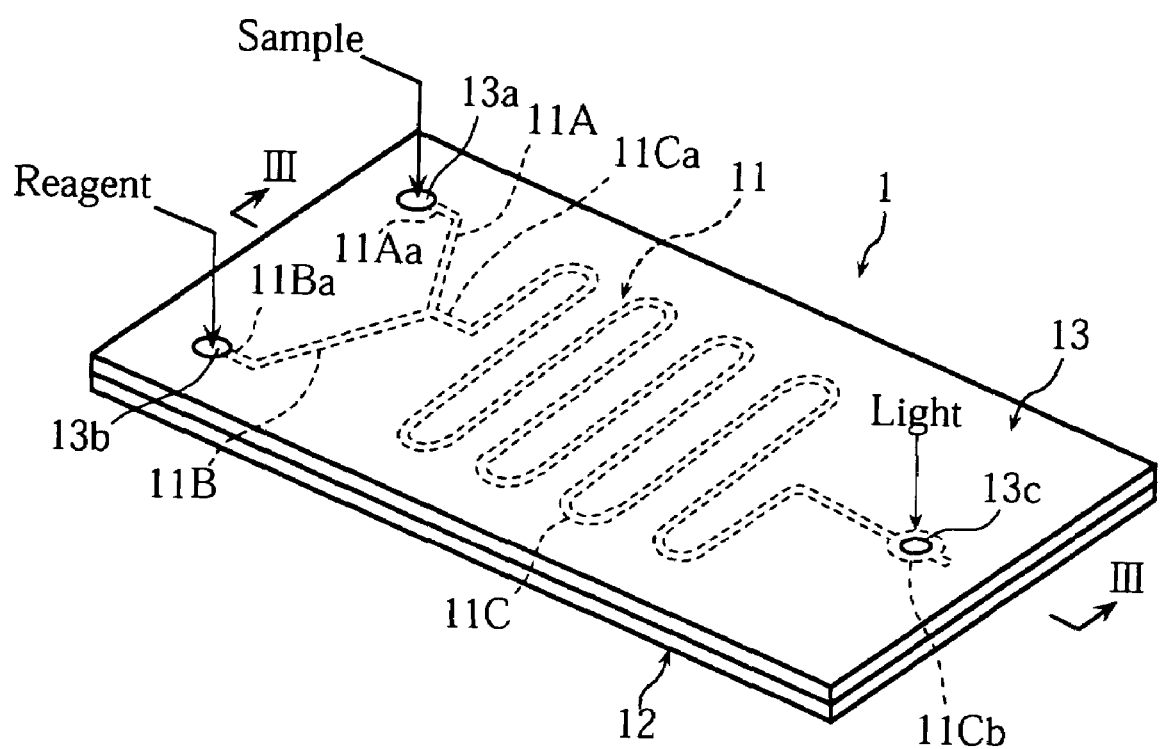
FIG. 2 is an entire perspective view showing an example of micro-device.
Figure 3:
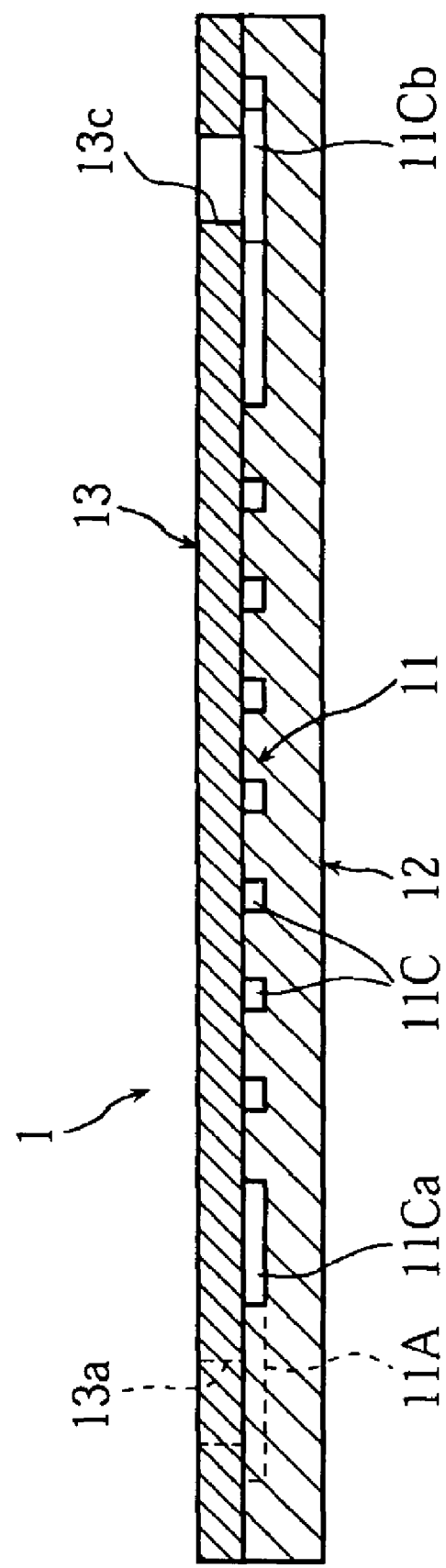
FIG. 3 is a sectional view taken along lines III-III in FIG. 2.

As the analytical tool 1, an analytical tool as shown in FIGS. 2 and 3 may be used. The analytical tool 1 shown in these figures is constituted as a micro-device for analyzing a sample based on a minute amount of sample. The micro-device, serving to provide a reaction field, includes a substrate 12 formed with a minute flow path 11 and a cover 13 stacked on the substrate to cover the flow path 11.

The flow path 11 includes a sample introduction portion 11A, a reagent introduction portion 11B and a reaction flow portion 11C. The sample introduction portion 11A and the reagent introduction portion 11B are connected to an end 11Ca of the reaction flow portion 11C. The reaction flow portion 11C meanders to have a long flow length. The reaction flow portion 11C has an another end 11Cb serving as a measurement portion which is to be irradiated with light emitted from the measurement light source 21 and from the heating light source 23 (See FIG. 1).

The cover 13 is formed with a sample introduction port 13a, a reagent introduction port 13b and an air discharge hole 13c. The sample introduction port 13a, the reagent introduction port 13b and the air discharge hole 13c are provided at locations corresponding to an end 11Aa of the sample introduction portion 11A, an end 11Ba of the reagent introduction portion 11B and the end 11Cb of the reaction flow portion 11C, respectively.

In the micro-device 1, two liquids, i.e. a sample and a reagent for reaction. However, use may be made of a micro-device which is capable of mixing three or more liquids and formed with a plurality of flow paths for constituting a plurality of reaction systems.

In analyzing a sample using the micro-device 1, the sample and the reagent are introduced through the sample introduction port 13a and the reagent introduction port 13b, respectively. The sample and the reagent move through the sample introduction portion 11A and the reagent introduction portion 11B by capillary action and merge at the reaction flow portion 11C. As a result, the sample and the reagent start reaction. The sample and the reagent, while undergoing reaction, move through the reaction flow portion 11C toward the air discharge hole 13c and finally reach the measurement portion 11Cb.

The temperature measurer 26 shown in FIG. 1 measures the temperature of the reaction solution (liquid component 10) with time after the solution has reached the measurement portion 11Cb. The measurement results are transmitted to the computing unit 24 and utilized as the basis for the computation in the computing unit 24.

In the computing unit 24, the actually measured temperature is compared with a prescribed target temperature of the liquid component 10, and the controlled variables for the heating light source 23 (e.g. the lighting time and the strength of light emission of the heating light source 23) are computed when the measured temperature is lower than the target temperature by a difference greater than a predetermined value. This computation can be performed by applying the measured temperature to a predetermined calculation formula, for example. The computation results obtained at the computing unit 24 are transmitted to the controller 25.

In accordance with the computation results, the controller 25 causes the heating light source 23 to light for a required period of time at a required strength. As a result, the temperature of the liquid component 10 is raised by an amount corresponding to the difference between the measured temperature and the target temperature. On the other hand, when the measured temperature is higher than the target temperature, the controller 25 turns off the heating light source 23. Such control for turning ON/OF is repetitively performed by feeding back the measurement results obtained by the temperature measurer 26.

The control of the heating light source 23 may be performed based on the ambient temperature around the liquid component 10. Specifically, the relationship between ambient temperatures and controlled variables of the heating light source 23 for heating the liquid component 10 to the target temperature is examined in advance. The relationship is converted into a table or a function and then stored in the computing unit 24, for example. Then, the controlled variable is determined based on the ambient temperature measured by the temperature measurer 26 and with reference to the above relationship (table or function), and the heating light source 23 is controlled in accordance with the controlled variable.

With this controlling method, the temperature adjustment may be performed by a single controlling operation for e.g. the heating light source 23, instead of repetitively controlling the heating light source.

When the temperature adjustment of the liquid component 10 is performed by utilizing light energy as is in the above embodiment, the liquid component can be directly heated. Therefore, the supplied energy can be utilized efficiently, which provides an advantage in terms of power consumption. In this case, an LD or an LED may be used as the light source, and therefore the temperature of the liquid component can be raised sufficiently by a small battery used as the internal power source without considerably shortening the life of the battery. Therefore, even in a small analyzing device, the temperature adjustment of the liquid component can be performed by utilizing the internal power source and without increasing the size of the device. Since the temperature adjustment can be performed by utilizing the internal power source, connection to an external power source is not necessary, and an adapter is dispensable. Thus, in carrying the analyzing device, an adapter need not be carried, which is convenient.

The present invention is not limited to the foregoing embodiment and may be modified in various ways. For example, although an analyzing device for performing analysis based on the light reflected after impinging on the liquid component has been exemplarily described, the present invention is also applicable to an analyzing device for analyzing the liquid component based on the transmitted light. The temperature adjustment may not be performed only for the liquid component at the measurement portion 11Cb. In addition to this or in place of this, the same may be performed for at least one of the liquid components present at the sample introduction portion 11A, the reagent introduction portion 11B and the reaction flow portion 11C.

Figure 4:
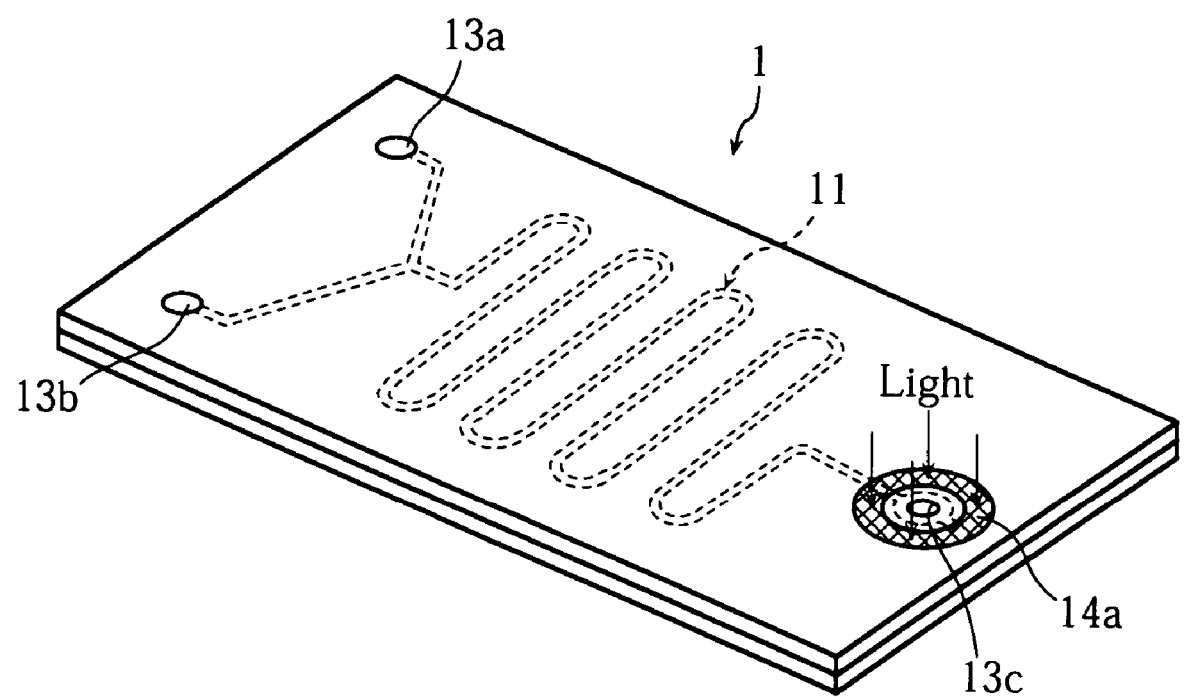
FIG. 4 is a perspective view of a micro-device for describing another example of method for raising the temperature of a liquid component.
Figure 5:
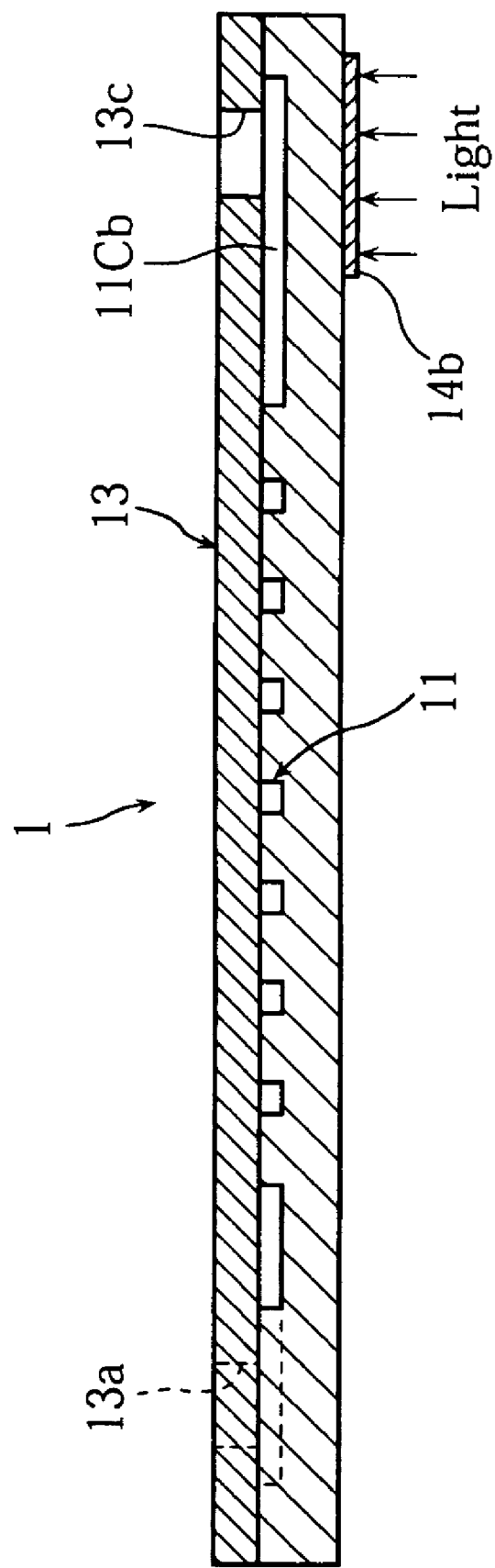
FIG. 5 is a sectional view of a micro-device for describing still another example of method for raising the temperature of a liquid component.

As shown in FIGS. 4 and 5, light energy may not be directly supplied to the liquid component but may be supplied indirectly to the liquid component. In the example shown in FIG. 4, a temperature raise region 14a is provided around the air discharge hole 13c. In the example shown in FIG. 5, a temperature raise region 14b is provided directly below the measurement portion 11Cb (liquid component). In these examples, light energy is applied to the temperature raise regions 14a, 14b to heat and raise the temperature thereof, and the thermal energy is conducted to the liquid component, whereby the temperature of the liquid component is raised.

As the material of temperature raise regions 14a, 14b, any material can be used as long as it can absorb light and conduct the energy to the liquid component. Accordingly, the material can be selected from a wide range. Also, with the temperature raising method, the wavelength of the light to be emitted, i.e. the light source can be selected depending on the light absorption characteristics of the material constituting the temperature raise regions 14a, 14b. Thus, as compared with the method of supplying light energy directly to the liquid component (See FIG. 1), the light source can be advantageously selected from a wider range.

The configuration and location of the temperature raise regions 14a, 14b are not limited to those shown in FIGS. 4 and 5. Further, the temperature raising may be performed by the combination of the method of directly heating the liquid component and the method of indirectly heating the liquid component.

Figure 6:
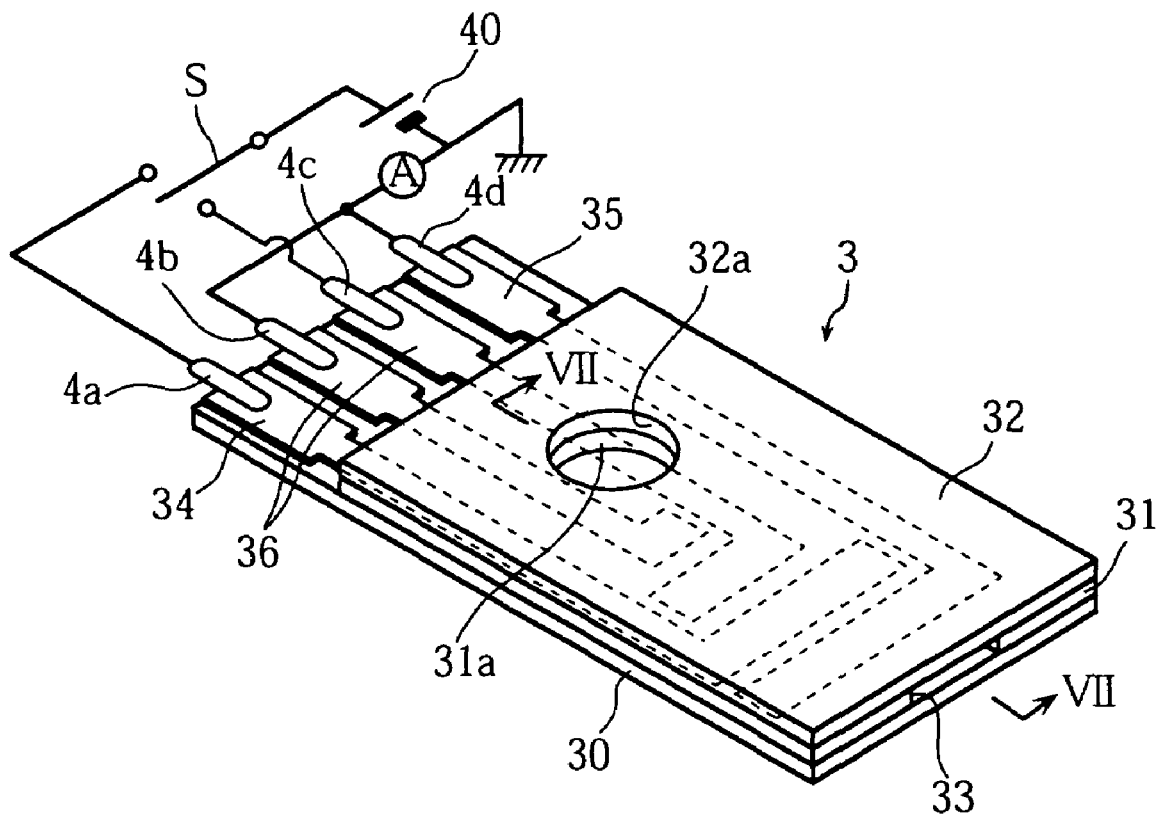
FIG. 6 is an entire perspective view showing another example of analytical tool to which the present invention is applicable.
Figure 7:
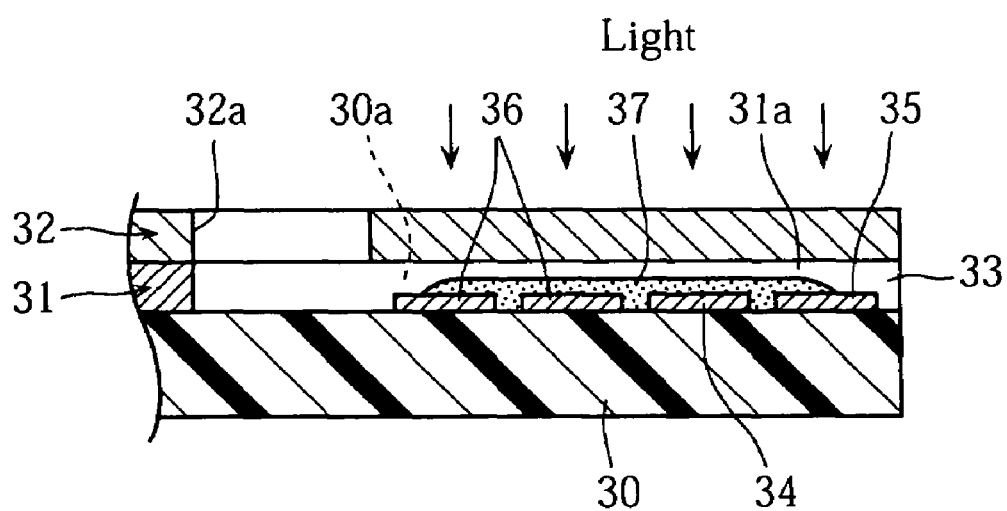
FIG. 7 is a sectional view taken along lines VII-VII in FIG. 6.

The present invention is not limited to an analyzing device for performing analysis by an optical method but is also applicable to an analyzing device for performing analysis by an electrochemical method. For example, the present invention is also applicable to a device in which the biosensor 3 shown in FIGS. 6 and 7 is mounted as an analytical tool so that the device performs analysis of a sample based on the responsive current when a voltage is applied.

The illustrated biosensor 3 includes a substrate 30 on which a capillary 30a is provided. For producing the capillary 30a, a cover 32 formed with a hole 32a is stacked on the substrate 30 via a spacer 31 formed with a slit 31a. The capillary 30a has a sample introduction port 33 at an end and is internally provided with a solid reagent 37. The sample introduced through the capillary introduction port 33 travels through the capillary 30a toward the hole 32a by capillary action while dissolving the sample 37.

An operative electrode 34 as a measurement electrode, a counterpart electrode 35, and a pair of detection electrodes 36 are formed on the substrate 30. The analyzing device includes measurement terminals 4a, 4b and detection terminals 4c, 4d for coming into contact with the electrodes 34-36, respectively. The terminals 4b, 4d are connected to ground, whereas the terminals 4a, 4c are connectable to a power source 40. By operating the switch S, selection can be made between a mode in which the power source 40 provides a potential difference between the operative electrode 34 and the counterpart electrode 35 and a mode in which the power source provides a potential difference between the paired detection electrodes 36.

In the analyzing device, a voltage may be applied to the reaction solution of the sample and the reagent 37. As a result, electron transfer occurs between the reaction product and the electrode, and the resulting responsive current is measured.

With such an arrangement, a reaction system is produced at the capillary 30a of the biosensor 3. Light energy is supplied to the reaction system for heating it and adjusting the temperature of the system. It should be noted here that the reaction system is provided between the substrate 30 and the cover 32. Thus, when light energy is supplied directly to the reaction system, it is preferable to reduce the amount of light absorbed by the substrate 30 and the cover 32 by making the substrate 30 and the cover 32 of a material which is less likely to absorb the light emitted from the light source. As readily understood, the biosensor 3 shown in FIG. 6 and the corresponding analyzing device are merely an example. The present invention is also applicable to a device which performs analysis of a sample by an electrochemical method differing from that described above.

The analytical tool to which the present invention is applicable is not limited to that for moving the sample and the reagent by capillary action. For example, their movement may be effectuated by electrophoresis, as shown in FIG. 8A, or by the motive power of an external pump.

Figure 8A:
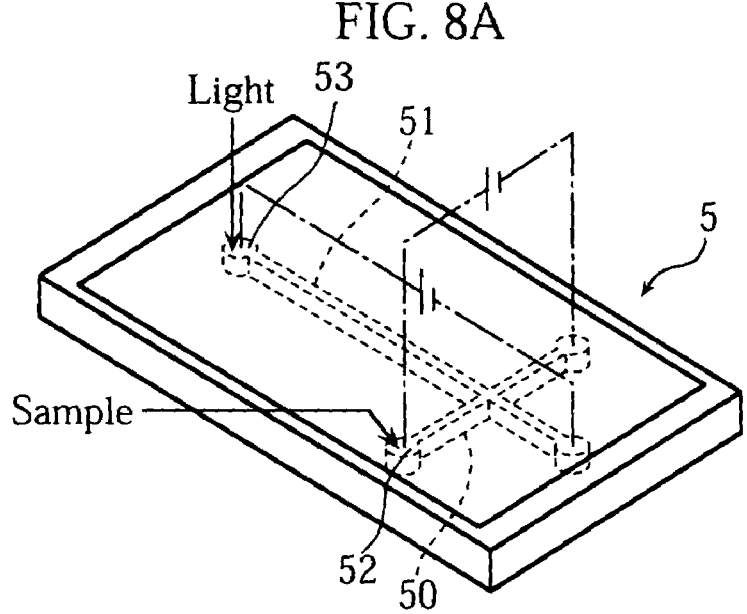
FIGS. 8A-8C each is an entire perspective view showing still another example of analytical tool to which the present invention is applicable.

The analytical tool 5 shown in FIG. 8A includes two flow paths 50, 51 intersecting each other. A migration buffer is loaded in each of the flow paths 50, 51. In analysis with the analytical tool 5, a potential difference is applied between opposite ends of each flow path 50, 51. Thus, the sample introduced through the sample introduction port 52 is caused to travel through the flow path 51 toward the measurement portion 53 while undergoing reaction in the flow path 51.

Figure 8B:
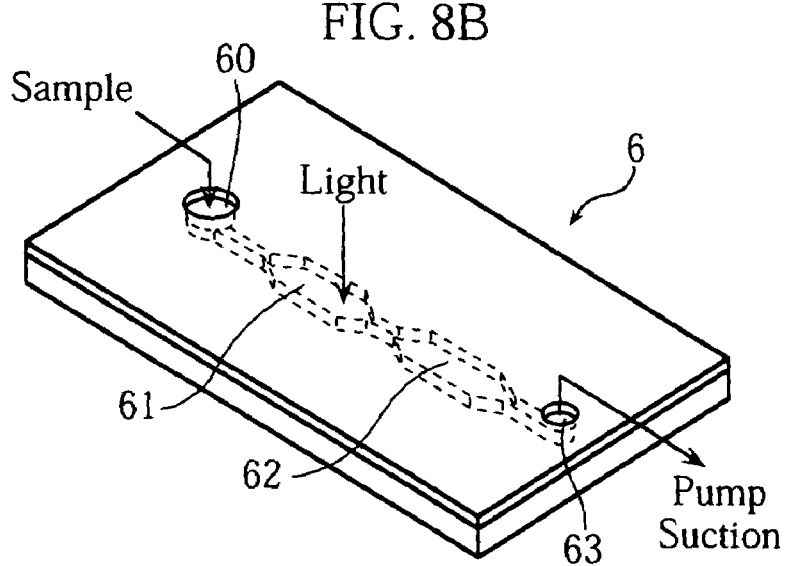

The analytical tool 6 shown in FIG. 8B includes a sample introduction portion 60, a reaction flow portion (measurement portion) 61, a discharged liquid storage portion 62 and a suction portion 63, all of which are arranged in a row. In the analytical tool 6, the suction portion 63 is connected to an external pump so that the sample is moved by the power of the pump. Alternatively, the analytical tool may incorporate a micropump which utilizes e.g. a piezoelectric element so that the sample or any other substance is moved by the micropump.

Figure 8C:
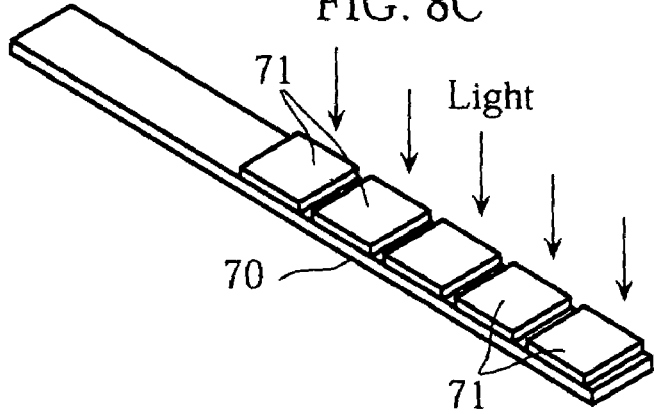
Figure 9A:
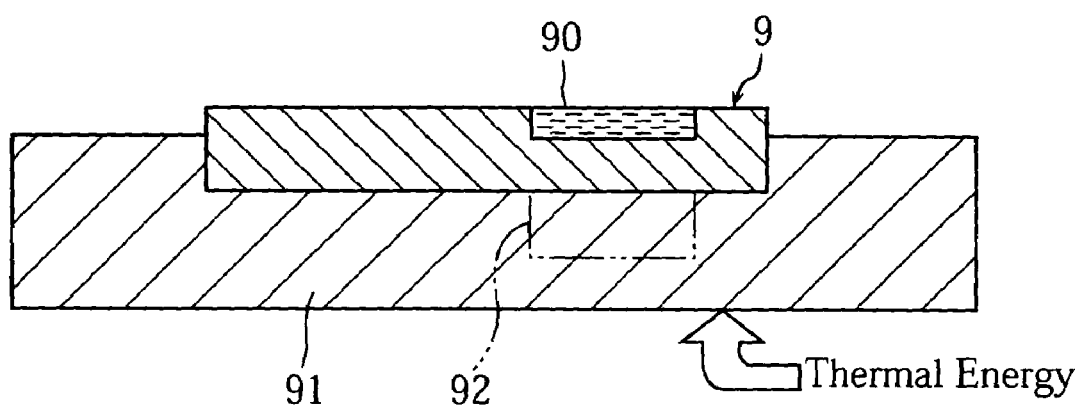
FIGS. 9A and 9B each is a sectional view showing a principal portion of an analyzing device for describing a prior art temperature adjustment method.
Figure 9B:
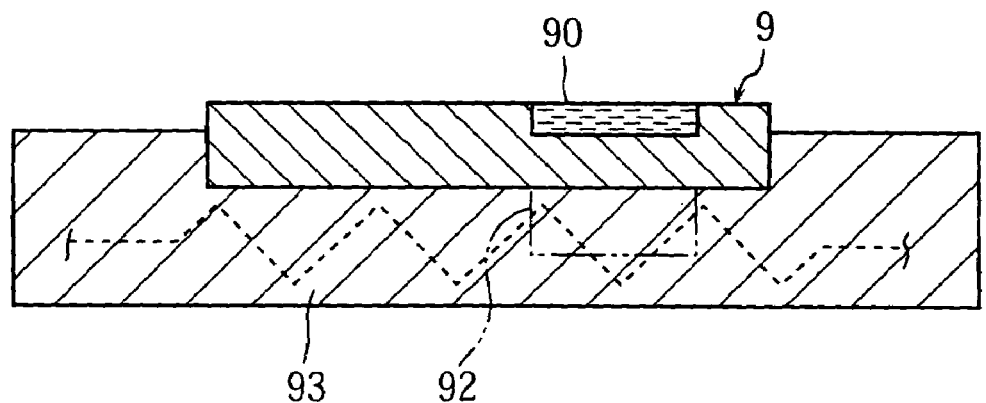

As shown in FIG. 8C, the analytical tool may include a strip base member 70, and solid reagent pads 71 provided on the base member. The number of reagent pads 71 is not limited to that shown in the figure.

The invention claimed is:

1. A temperature adjustment method with respect to an analytical tool used for analyzing a sample, the method for adjusting temperature of a liquid component retained in the analytical tool, comprising:
    heating the liquid component by utilizing light energy from a light source in raising the temperature of the liquid component;
    examining, in advance, a relationship between an ambient temperature around the liquid component and a controlled variable for the light source necessary for raising the temperature of the liquid component to a target temperature; and
    determining the controlled variable of the light source based on a measured ambient temperature and the relationship, the light source being controlled in accordance with the determined controlled variable.

2. The temperature adjustment method according to claim 1, wherein the temperature raising of the liquid component is performed by directly supplying the light energy to the liquid component.

3. The temperature adjustment method according to claim 2, wherein the light source emits light of a wavelength having high absorptance to water.

4. The temperature adjustment method according to claim 3, wherein the light source emits infrared rays or near-infrared rays.

5. The temperature adjustment method according to claim 1, wherein the temperature raising of the liquid component is caused by thermal energy transferred from a temperature raise region adjacent to the liquid component the light energy being supplied to the temperature raise region.

6. The temperature adjustment method according to claim 1, wherein the light source comprises a laser diode or a light-emitting diode.

7. The temperature adjustment method according to claim 1, wherein the temperature adjustment of the liquid component is performed by repetitive control of light energy emitted from the light source, the repetitive control being based on feedback of results obtained by monitoring the temperature of liquid component.

8. The temperature adjustment method according to claim 1, wherein the analytical tool analyzes the sample based on a response upon light irradiation.

9. The temperature adjustment method according to claim 8, wherein the light source is utilized for irradiating the analytical tool with light and for performing the analysis of the sample.

10. The temperature adjustment method according to claim 1, wherein the liquid component as a temperature adjustment target is no more than 100 μL.

11. The temperature adjustment method according to claim 1, wherein the analytical tool comprises a micro-device.

12. A temperature adjustment method with respect to an analytic tool used for analyzing a sample, the method for adjusting temperature of a liquid component retained in the analytical tool, comprising:
heating the liquid component by utilizing light energy from, a light source in raising the temperature of the liquid component;
wherein the analytical tool analyzes the sample based on a response upon light irradiation; and
wherein the light source is utilized for irradiating the analytical tool with light and for performing the analysis of the sample.

13. An analyzing device having temperature adjustment function, wherein the device utilizes an analytical tool with a sample retained thereon for analyzing the sample, and
wherein the device comprises a measurement light source for directing measurement light toward the sample in a first direction,
a heating light source for-directing heating light toward the sample in a second direction different from the first direction,
a temperature measurer for measuring temperature of the sample or ambient temperature around the sample, and
a light source controller for controlling the heating light source based on the measurement by the temperature measurer.

14. The analyzing device according to claim 13, wherein the analytical tool analyzes the sample based on a response upon light irradiation from the measurement light source.

15. The analyzing device according to claim 13, further comprising a light receiver for receiving light from the sample, the beating light source is arranged between the measurement light source and the light receiver.

16. The analyzing device according to claim 13, wherein the heating light source emits light of a wavelength having high absorptance to water.

17. The analyzing device according to claim 16, wherein the heating light source emits infrared rays or near-infrared rays.

18. The analyzing device according to claim 13, wherein the heating light source comprises a laser diode or a light-emitting diode.

19. The analyzing device according to claim 13, wherein the analytical tool comprises a micro-device.

* * * * *